United States Patent [19]

Anderson et al.

[11] Patent Number: 5,039,810

[45] Date of Patent: Aug. 13, 1991

[54] PYRIDYL PROPENOATE COMPOUND

[75] Inventors: Kenneth Anderson, Bury; John M. Clough, Marlow; Christopher R. A. Godfrey, Bracknell, all of England

[73] Assignee: Imperial Chemical Industries PLC, London, England

[21] Appl. No.: 258,661

[22] Filed: Oct. 17, 1988

[30] Foreign Application Priority Data

Oct. 15, 1987 [GB] United Kingdom ................ 8724251

[51] Int. Cl.$^5$ ............................................ C07D 213/61
[52] U.S. Cl. .................................................... 546/341
[58] Field of Search ................ 546/290, 301, 342, 341

[56] References Cited

U.S. PATENT DOCUMENTS

| | | | |
|---|---|---|---|
| 3,651,123 | 3/1972 | Moyle et al. | 560/57 |
| 3,707,470 | 12/1972 | Sawa et al. | 260/285 |
| 4,414,391 | 11/1983 | Cartwright et al. | 546/302 |
| 4,529,438 | 7/1985 | Lee | 71/94 |
| 4,561,882 | 12/1985 | Lee | 71/94 |

FOREIGN PATENT DOCUMENTS

| | | |
|---|---|---|
| 0050019 | 4/1982 | European Pat. Off. . |
| 0057057 | 8/1982 | European Pat. Off. . |
| 0243012 | 10/1987 | European Pat. Off. . |
| 2117826 | 4/1970 | Fed. Rep. of Germany . |
| 7075947 | 5/1982 | Japan . |
| 7075948 | 5/1982 | Japan . |
| 2078743 | 1/1982 | United Kingdom . |

OTHER PUBLICATIONS chemical Reviews, 38:139 (1946) and 64:613 (1964).
Chemical Abstracts, 77 (1972) 100667f and 79 (1973) 115261j.
Houben-Weyl, "Methoden der Organischen Chemie", 4th Ed., vol. VI/3, 1965, Chemical Abstracts, vol. 31, No. 6, No. 1 809q (Mar. 20, 1937).
Derwent Abstracts, J57075948 (1980).
March, J., Advanced Organic Chemistry, 3rd Ed., Wiley & Sons (1987), pp. 342–343, 589.

Primary Examiner—C. Warren Ivy
Assistant Examiner—Zinna Northington-Davis
Attorney, Agent, or Firm—Cushman, Darby & Cushman

[57] ABSTRACT (E)-methyl 2-(2-chloropyrid-3-yl)-3-methoxypropenoate.

1 Claim, No Drawings

PYRIDYL PROPENOATE COMPOUND

This invention relates to a process for the preparation of derivatives of propenoic acid which are useful as fungicides or as chemical intermediates in the preparation of fungicides.

According to the invention, there is provided a process for the preparation of a compound of general formula (I):

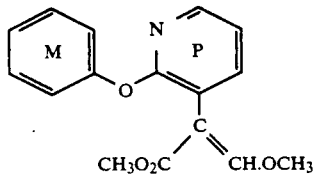

wherein the aromatic rings M and P optionally carry one or more substituents which are not reactive under the conditions of the process, which comprises reacting a compound of general formula (II):

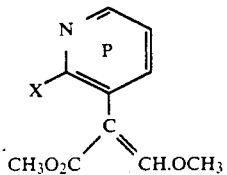

wherein X is halogen (preferably iodine, chlorine or bromine) or other good leaving group with a phenol of general formula (III):

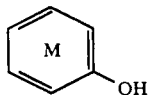

in the presence of a base, or with a salt of the phenol (III), preferably in the presence of a catalyst which comprises a suitable transition metal or transition metal salt or compound or a mixture thereof.

By this process, compounds of general formula (I) can be obtained by reaction of compounds (II) with salts derived from phenols of general formula (III) by prior treatment of the phenols with base. In this aspect of the invention, the additional presence of a base during the coupling reaction is not required.

In compound (II), other good leaving groups which X may be include $C_{1-4}$ alkylsulphonyl, optionally substituted aryl(suitably phenyl)sulphonyl and nitro.

A solvent may be employed in carrying out the process of the invention. Suitable solvents are those in which both compounds (II) and (III) (or salts derived therefrom) are soluble or partially soluble and which do not react with either of these substrates under the condition of the reaction. Solvents which may be used include dipolar aprotic solvents such as N,N-dimethylformamide, dimethylsulphoxide, N,N-dimethylacetamide and methylisobutylketone. In certain cases, when either of the substrates is a liquid under the conditions of the reaction, it is possible to perform the reaction in the absence of an added solvent.

Suitable bases for use in the process are those which act either by abstraction of the phenolic proton of compound (III) prior to reaction with substrate (II) or by neutralisation of any acid produced during the reaction, without reacting significantly with substrate (II) or product (I). An example of such a base is anhydrous potassium carbonate.

Suitable transition metals or transition metal salts or compounds which may catalyse the process include copper metal, copper salts and compounds and nickel salts and compounds, such as copper bronze and copper (I) chloride, which may be used separately or in admixture (see, for example, A. A. Moroz and M. S. Shvartsberg, *Russian Chemical Reviews*, 1974, 43 (8), 679–689).

The process may be conducted over a wide range of temperatures. In practice, the temperature will be chosen so that reaction occurs at a reasonable and convenient rate. This will usually be in the range 100° C. to 200° C. depending on the reactivity of the substrates (II) and (III) and the nature of the catalyst.

Typically, the compound (II) is treated with a phenol in the presence of potassium carbonate in N,N-dimethylformamide at about 150° C. At the end of the reaction (as evidenced by GC or TLC analysis) the product is isolated by extraction into ether followed by evaporation and recrystallisation (from a suitable solvent or solvent mixture). Alternatively the product may be purified by chromatography.

The presence of the propenoate double bond gives rise to geometric isomers of the compounds (I) and (II). These isomers are denoted by the commonly used terms (E) and (Z) according to the Cahn-Ingold-Prelog system which is fully described in the literature (see, for example, J. March, "Advanced Organic Chemistry", 3rd Edition, Wiley-Interscience, page 109 et seq). Either the (E)- or the (Z)- isomer of compounds of general formula (II) or mixtures thereof can be used as substrates in the process of the invention. Under the conditions of the reaction, the (Z)-isomer of compounds of general formula (II) usually undergoes stereomutation to the corresponding (E)-isomer, reaction then preceding to give compounds of general formula (I) of (E)-geometry. That is, compounds of formula (I) of (E)-geometry are usually formed irrespective of the geometry of the precursors of formula (II).

The process of the invention is of special interest in the preparation of fungicidal compounds; for instance, those described in EP-A-0243012 and, in particular, those compounds of general formula (IV)

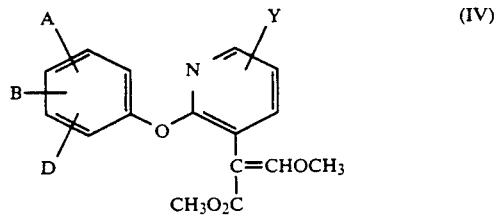

wherein A, B, D and Y, which may be the same or different, are hydrogen or halogen atoms, or optionally substituted alkyl, optionally substituted alkenyl, optionally substituted aryl, optionally substituted heteroaryl, optionally substituted alkynyl, optionally substituted alkoxy, optionally substituted aryloxy, optionally substituted heteroaryloxy, optionally substituted arylalkoxy, optionally substituted acyloxy, optionally substituted sulphonyloxy, optionally substituted amino, optionally substituted arylazo, acylamino, nitro, cyano, $-CO_2R^1$, $-CONR^2R^3$, $-COR^4$, $-CR^5=NR^6$, or $-N=CR^7R^8$ groups, or the groups A and B, when they are in adjacent positions on the phenyl ring, may join to form a fused ring, optionally containing one or more heteroatoms; and $R^1$, $R^2$, $R^3$, $R^4$, $R^5$, $R^6$, $R^7$ and $R^8$, which may be the same or different, are hydrogen atoms or alkyl, cycloalkyl, alkenyl, alkynyl, optionally substituted aryl, optionally substituted heteroaryl, optionally substituted aralkyl, or cycloalkylalkyl groups.

The process may also be used to prepare chemical intermediates useful in the preparation of fungicides.

The substrate of general formula (II) may be prepared according to processes outlined in EP-A-0243012. The substrate, (E)-methyl 2-(2-chloropyrid-3-yl)-3-methoxypropenoate, whose preparation is specifically described herein, forms another aspect of the present invention.

Compounds of general formula (III) can be prepared by known methods as described in the chemical literature.

The following example illustrates the invention. Throughout this example, reactions involving water- or air-sensitive intermediates were performed under a nitrogen atmosphere in dry solvents, the term 'ether' refers to diethyl ether, magnesium sulphate was used to dry solvents, solutions were concentrated under reduced pressure, and chromatography was performed on columns of silica gel. Unless otherwise stated, NMR spectra were recorded at 270MHz using deuteriochloroform solutions and tetramethylsilane as the internal standard. Where shown, spectroscopic data are selective; no attempt is made to list every absorption in all cases.

The following abbreviations are used:
NMR—Nuclear magnetic resonance
s—Singlet
mp—Melting Point
DMF—N,N-dimethylformamide
TLC—Thin layer chromatography

EXAMPLE 1

This example illustrates the preparation of (E)-methyl 2-(2-(3-fluorophenoxy)pyrid-3-yl)-3-methoxypropenoate ((IV), A=3-F, B=D=Y=H).

To an ice-cold stirred suspension of petrol-washed sodium hydride (1.04 g, 50% dispersion in oil, 22 mmol) in DMF (16 ml) was added a solution of methyl 2-chloropyrid-3-ylacetate (2 g, 11 mmol) and methyl formate (12.95 g, 0.22 mol) in DMF (8 ml). The reaction mixture was allowed to warm to room temperature and stirring continued until TLC analysis showed that no starting material remained (ca 3 hours). The reaction mixture was poured into water and then acidified with dilute hydrochloric acid. The solution was extracted repeatedly with ether and the combined extracts dried, filtered and evaporated. The residue was redissolved in DMF and then treated with dimethyl sulphate (1.32 g, 10.5 mmol) and anhydrous potassium carbonate (1.52 g, 11 mmol) at room temperature.

The reaction mixture was stirred for 2 hours, diluted with water and then repeatedly extracted with ether. The combined ether extracts were dried, filtered and evaporated to afford a yellow oil. Chromatography on silica (eluent petrol-ether, 50:50) gave (E)-methyl 2-(2-chloropyrid-3-yl)-3-methoxypropenoate as a white waxy solid (0.9 g, 36%); mp 39°–40° C.; Infrared max 1711, 1638 cm$^{-1}$; $^1$H NMR delta 3.74 (3H,s), 3.89 (3H,s), 7.21–7.26 (1H), 7.55–7.57 (1H), 7.60 (1H,s), 8.32–8.36 (1H).

(E)-methyl 2-(2-chloropyrid-3-yl)-3-methoxypropenoate (0.1 g, 0.4 mmol), 3-fluorophenol (0.045 g, 0.4 mmol) and potassium carbonate (0.028 g, 0.2 mmol) were heated together at ca 180° C. in the presence of catalytic amounts of copper(I) chloride and copper bronze.

After 4 hours, the reaction mixture was cooled and the residue dissolved in a small amount of dichloromethane. Chromatography on silica (eluent petrolether, 60:40) gave unreacted (E)-methyl 2-(2-chloropyrid-3-yl)-3-methoxypropenoate (0.041 g, 41%) and (E)-methyl 2-(2-(3-fluorophenoxy)pyrid-3-yl)-3-methoxypropenoate as a clear oil (0.02 g, 17%); Infrared max 1710, 1638 cm$^{-1}$; $^1$H NMR (delta) 3.69 (3H,s), 3.85 (3H,s), 6.79–6.90 (3H), 7.02–7.08 (1H), 7.26–7.34 (1H), 7.58 (1H,s), 7.62–7.64 (1H), 8.11–8.15 (1H); m/e 303 (M+).

We claim:
1. (E)-methyl 2-(2-chloropyrid-3-yl)-3-methoxypropenoate.

* * * * *